United States Patent [19]

Nakatomi et al.

[11] Patent Number: 4,547,374

[45] Date of Patent: Oct. 15, 1985

[54] SACCHAROMYCES SPECIES FD 612 AND THE UTILIZATION THEREOF IN BREAD PRODUCTION

[75] Inventors: Yasuo Nakatomi, Chiba; Hiraku Saito, Osaka; Akihiro Nagashima, Chiba; Fumio Umeda, Saitama, all of Japan

[73] Assignee: Oriental Yeast Co., Ltd., Tokyo, Japan

[21] Appl. No.: 491,664

[22] Filed: May 5, 1983

[30] Foreign Application Priority Data

May 21, 1982 [JP] Japan .................................. 57-84699

[51] Int. Cl.$^4$ .......................... A21D 8/04; C12N 1/18; C12R 1/85
[52] U.S. Cl. ...................................... 426/19; 426/62; 435/172.1; 435/256; 435/940
[58] Field of Search .................. 435/940, 942; 426/18, 426/19, 62, 27

[56] References Cited

U.S. PATENT DOCUMENTS

| | | | |
|---|---|---|---|
| 3,375,117 | 3/1968 | Schremmer | 426/62 |
| 3,394,008 | 7/1968 | Lodder et al. | 426/19 |
| 3,894,155 | 7/1975 | Ono et al. | 426/19 |
| 3,901,975 | 8/1975 | Taguchi et al. | 426/62 |
| 4,374,151 | 2/1983 | Lindstrom et al. | 426/62 |

OTHER PUBLICATIONS

Godkin et al., Fermentation Activity and Survival of Yeast in Frozen Fermented and Unfermented Dough, 1949, pp. 139-146.

Primary Examiner—Raymond Jones
Assistant Examiner—Marianne M. Cintins
Attorney, Agent, or Firm—Browdy and Neimark

[57] ABSTRACT

Saccharomyces species FD 612 (FERMBP-742), which has been bred by selective hybridizations, has freeze-resistance and is useful as a baker's yeast in bread production in which a dough is prepared utilizing flour and Saccharomyces species FD 612 as the leavening agent. The dough thus prepared is thereafter frozen, thawed after frozen-storage, fermented, and baked to result in bread of good quality.

4 Claims, 1 Drawing Figure

SACCHAROMYCES SPECIES FD 612 AND THE UTILIZATION THEREOF IN BREAD PRODUCTION

FIELD OF THE INVENTION

The present invention relates to an improved baking yeast and an improved baking process using such yeast.

BACKGROUND OF THE INVENTION

Most Baker's Yeasts presently on the market are carefully selected strains of *Saccharomyces cerevisiae*. They have the characters with a good yield, good keeping qualities, good dispersibility and a powerful and constant gassing power in dough.

However, in recent years, due to circumstances in the baking industry, there has been put into practice the method in which dough is frozen and stored and thawed before baking. When using a frozen dough, there is a problem as to the gassing power of baker's yeasts which have undergone such freeze-storage. When conventional baker's yeasts belonging to *Saccharomyces cerevisiae* are used for a frozen dough, for example, being stored at $-20°$ C. for one week or more, the yeasts will suffer freeze-injury which leads to a considerable lowering of their gassing power after thawing. Therefore, such a frozen dough fails to become a soft and full bread, even though it is subjected to fermentation and baking.

Due to such circumstances, strains belonging to *Saccharomyces rosei* have been developed as a freeze-resistant baker's yeast. It has, however, been shown that strains belonging to *Saccharomyces rosei* cannot ferment maltose and do not show sufficient gassing power under a low concentration of sugar and therefore are inferior for use as a baker's yeast in the baking of white bread, hard roll, etc., as compared to conventional baker's yeasts belonging to *Saccharomyces cerevisiae*.

SUMMARY OF THE INVENTION

Accordingly, it is an object of the present invention to solve the problems of the prior art.

It is more specifically an object of the present invention to obtain a yeast having the same excellent gassing power as conventional baker's yeasts belonging to *Saccharomyces cerevisiae* and, in addition, being capable of long storage in a frozen dough without a decrease in gassing power.

These and other objects have been attained in accordance with the present invention by means of a novel baker's yeast, i.e., Saccharomyces species FD 612 and the utilization thereof.

More specifically, the present invention relates to Saccharomyces species FD 612 which has excellent freeze-resistance and in addition is very excellent as a baker's yeast. The present invention further relates to a process for bread production by the use of Saccharomyces species FD 612.

BRIEF DESCRIPTION OF THE DRAWING

The drawing is a distribution diagram showing the production of Saccharomyces species FD 612 of the present invention.

DETAILED DESCRIPTION OF PREFERRED EMBODIMENTS

Figure 1:
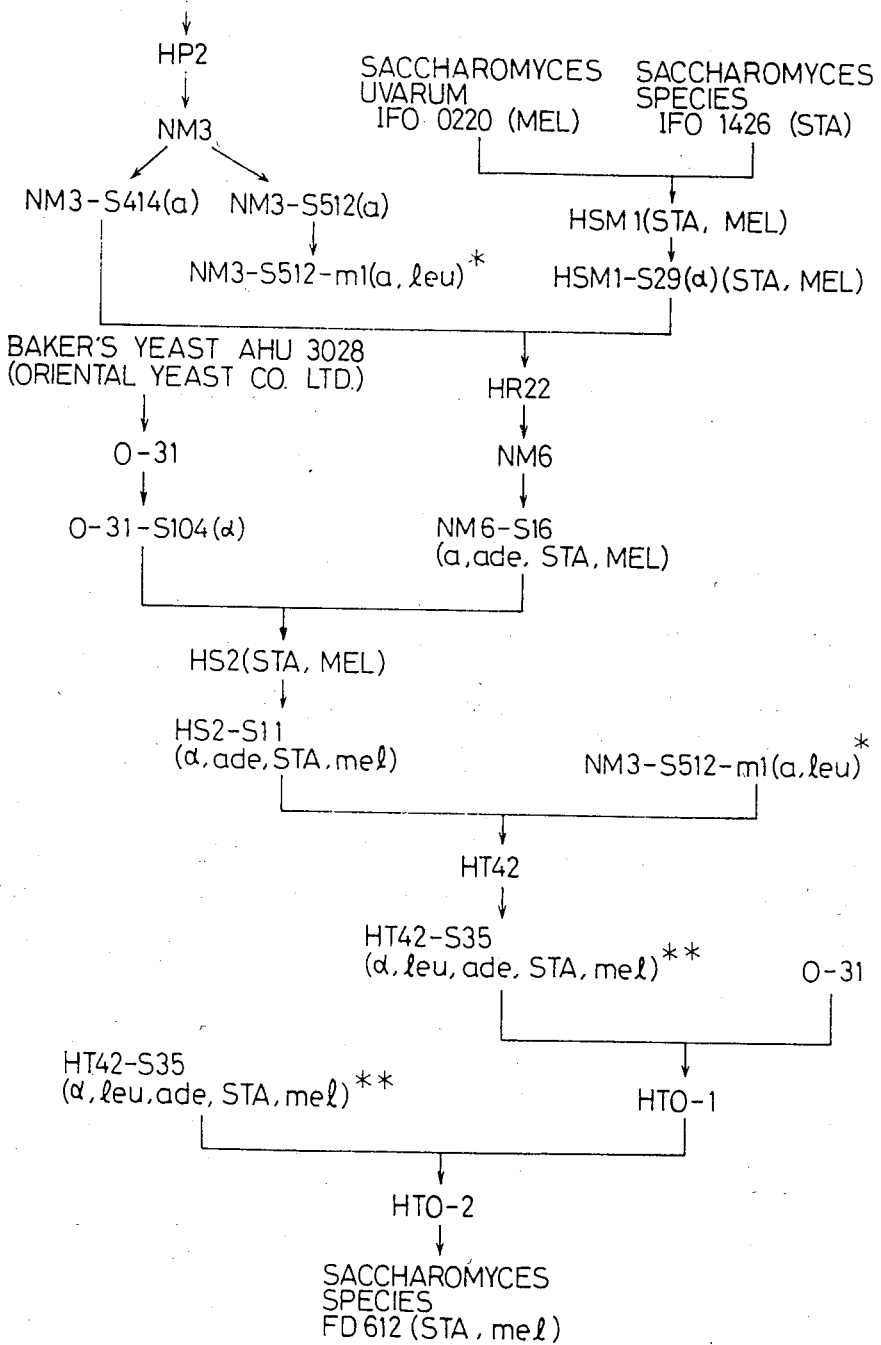

The present invention relates to Saccharomyces species FD 612 and the utilization thereof.

Saccharomyces species FD 612 of the present invention has been bred by selective hybridization between yeast AHU3028, and other yeast strains originating from *Saccharomyces uvarum* IFO 0220 and Saccharomyces species IFO 1426.

Due to the fact that Saccharomyces species FD 612 of the present invention has been produced by frequent uses of *Saccharomyces cerevisiae* in many matings, its taxonomic properties agree nearly with those of *Saccharomyces cerevisiae*, and Saccharomyces species FD 612 has an excellent activity for dough fermentation, which property is derived from *Saccharomyces cerevisiae*. In addition, it is considered that Saccharomyces species FD 612 must have been given an ability to utilize starch by Saccharomyces species IFO 1426. Saccharomyces species FD 612 has been deposited with the Fermentation Research Institute, Agency of Industrial Science and Technology under the deposition number of FERM BP-742 (formerly FERM P-6527).

The taxonomic properties of Saccharomyces species FD 612 are shown as follows:

(a) Growth state: Abundant growth on YM agar medium.
 A white, flat and smooth colony is formed thereon.
 A vegetative cell is $2-7\mu \times 2-9\mu$, circularelliptic, and multiplicates by budding.
(b) Spore formation: Ascospores are formed on a potassium acetate medium. A spore is circular.
(c) Physiological properties:
 (1) Optimum growth condition:
  pH: 4.5-6.0
  Temperature: $28°-30°$ C.
  Aerobic or anaerobic: Facultative aerobic
 (2) Conditions for growth:
  pH: 2.5-10.0
  Temperature: $3°-40°$ C.
  Aerobic or anaerobic: Growable under both
 (3) Nitrate assimilation: Negative
 (4) Vitamin requirement: Pantothenic acid and biotin are required.
(d) Carbon source utilization and fermentation:

| Carbon source | Utilization | Fermentation (Gas production) |
|---|---|---|
| D-arabinose | − | − |
| D-xylose | − | − |
| D-glucose | + | + |
| D-galactose | + | + |
| Maltose | + | + |
| Sucrose | + | + |
| Lactose | − | − |
| Melibiose | − | − |
| Trehalose | + | ± |
| Raffinose | + | ± |
| α-methyl-D-glucoside | + | + |
| Dextrin | + | ± |
| Soluble starch | + | − |
| Ethanol | + | |

± means "positive" in acid production and "negative" in gas production.

The segregation of auxotrophic traits are observed. That is, the segregant strains isolated from Saccharomyces species FD 612 show that the number ratio of strains requiring adenine is about 1:1, and that the number ratio of strains requiring leucine is about 1:1.

The process for breeding Saccharomyces species FD 612 of the present invention is shown in the pedigree (FIG. 1). A non-mater segregant NM3 (diploid) is selected from segregants of tetraploid HP2 which is originating from baker's yeast AHU3028. NM3 has a good gassing power in dough. Then the segregants NM3 s414 and NM3 s512 are obtained from NM3. On the other hand, strain HSM1 capable of utilizing both starch and melibiose is bred by crossing a segregant from *Saccharomyces uvarum* IFO 0220 with a segregant from Saccharomyces species IFO 1426 capable of utilizing starch. Further a segregant HSM1 s29 is isolated from HSM-1. Next a hybrid HR-22 is bred by crossing HSM1 s29 with NM3 s414. A non mater segregant NM6 is selected from the segregants of HR-22. Then a haploid NM6 s16 is isolated from NM6. Separately, a haploid 031 s104 is isolated from 031 which is commercially available baker's yeast (Oriental Yeast Co., Ltd.) originating from baker's yeast AHU3028. A hybrid HS2 is bred by crossing 031 s104 with NM6 s16. A haploid HS2 s11 is isolated from the hybrid HS2. A hybrid HT42 is bred by crossing HS2 s11 with NM3 s512 ml which is a mutant of strain NM3 s512. A haploid HT42 s35 is isolated from the hybrid HT42. A hybrid HTO-1 is bred by crossing HT42 s35 with 031 (RD) which is a respiration deficient strain of 031 (commercially available baker's yeast). Further the hybrid HTO-2 is bred by crossing HT42 s35 with HTO-1 (RD) which is a respiration deficient strain of HTO-1. Saccharomyces species FD 612 of this invention is selected from about 400 segregants of HTO-2. FD 612 has an excellent ability for bread production and an excellent freeze-resistance.

The isolations of spores mentioned above are carried out by the random spore-isolation method which is generally known. Namely, this method is carried out as follows: spores are formed by the use of a sporulation medium, and are homogenized by carrying out a homogenizing treatment. Heat treatment is then carried out at 60° C. for 10 minutes to kill vegetative cells, followed by smearing on a complete medium plate, cultivation at a suitable temperature, and separation and selections of formed colonies. The matings mentioned above are carried out by the Mass mating method or the Rare-mating method (J. Inst. 85, 286–289, R. S. Tubb) which are generally known. Variants are obtained by EMS treatment.

Saccharomyces species FD 612 thus obtained has the excellent properties of baker's yeast in its original condition and, in addition, has starch utilization capability and excellent freeze-resistance, and therefore is useful as a baker's yeast for all kinds of bread.

The yeast strains for comparative experiment were grown in a agitation-aeration vessel of 1000 ml working volume. The temperature of the culture maintained at 30° C. The yeast propagation took place by aerobic cultivations with incremental feeding of the cane molasses medium (25% cane molasses, inorganic nitrogen and phosphate), commonly used in practical production of baker's yeast (J. White: Yeast Technology, London, 1954). The yeast cells cultivated were collected by centrifugation and washed three times with water.

Bread production using the baker's yeast Saccharomyces species FD 612 is carried out in the same manner as a conventional bread production method. Namely, bread ingredients comprising flour, sugar, salt, shortening and the baker's yeast (Saccharomyces species FD 612) are mixed with water to prepare a dough.

In the present invention, the dough thus obtained is frozen at about −40° C. for 1 hour after a molding or after no molding, with a slight fermentation or with a sufficient fermentation or with no fermentation, and stored at −20° C. for one day—one year.

The frozen dough is thawed at 5° C. for about 15 hours or at room temperature for 1–2 hours, then, the dough is subjected to final proofing at 35° C. after a molding with a sufficient fermentation or after a supplemental fermentation or without any fermentation. In case of the dough had already molded, it is immediately subjected to final proofing. Then the dough is baked at 200°–210° C. for 20 minutes, to result in the production of bread.

Even after such a long freeze—storage, Saccharomyces species FD 612 still shows an excellent activity.

The test and examples of the present invention are as follows:

Test 1.

Saccharomyces species FD 612, FERM BP-742 (referred to as FD 612 hereinafter) and commercially available baker's yeast O-31 (Oriental Yeast Co., Ltd.) were respectively cultivated, and fermented at 30° C. in a 10% sucrose medium (Schultz-Atkins medium). Both cultivations were stopped when $CO_2$ gas was produced up to 55 ml respectively, and, immediately, each respective culture was put into a storage box of which the inner temperature was −40° C. The cultures were then thawed at room temperature after freeze-storage for one day, and dyed with methylene blue. The survival rates were determined by the following formula:

$$\text{Survival rate} = \frac{\text{Yeasts cells non-dyed with methylene blue} = \text{Number of yeast cells survived}}{\text{Total number of yeast cells counted}} \times 100$$

The results showed that the survival rate of FD 612 was 75.0% and that of commercially available baker's yeast was 29.8%.

Test 2.

The gassing powers (carbon dioxide gas m/2 hr) of FD 612, commercially available baker's yeast O-31 and *Saccharomyces rosei* AHU 3976 were examined by the use of three Schultz-Atkins mediums having dissolved sucrose of 10% (F(10)), maltose of 5% (Fm(5)) and sucrose of 40% (F(40)).

The results are shown in Table 1.

TABLE 1

| Strain | Gassing power in each medium ($CO_2$ ml/2 hr) | | |
|---|---|---|---|
| | F(10) | Fm(5) | F(0) |
| FD 612 | 154 | 73 | 87 |
| Commercially available baker's yeast (Oriental Yeast Co., Ltd.) | 160 | 60 | 94 |
| *Saccharomyces rosei* AHU 3976 | 102 | 0 | 82 |

EXAMPLE 1

White bread production using FD 612 was examined according to the following conditions and compared with that using, as a control, commercially available baker's yeast O-31 (Oriental Yeast Co., Ltd.).

| [Formula] | (%) |
| --- | --- |
| Bread flour | 100 |
| Salt | 2 |
| Sugar | 5 |
| Shortening | 6 |
| Nonfat dry milk | 2 |
| Yeast food | 0.2 |
| Water | 62 |
| Yeast (FD 612 or O-31) | 4 |

[Procedure]
(1) Mixing:
 1 minute at low speed,
 6 minutes at medium speed,
 2 minutes at high speed.
(2) Dough temperature out of mixer: 22° C.
(3) Fermentation: 15 or 90 minutes (at 28° C.)
(4) Scaling weight: 360 grams
(5) Freezing: 1 hour at −40° C.
(6) Storage: 2 weeks at −20° C.
(7) Thawing: 15 hours at 5° C.
(8) Molding: Immediately after thawing (Dough temperature is 5° C.)
(9) Final proofing: Until a height of 2 cm over from a pan (at 35° C.)

As shown in Table 2, the results were as follows: When the white bread were produced in the same manner as conventional bread production method, the loaves produced by using FD 612 showed a quality hardly inferior to that of the loaves of produced by using conventional *Saccharomyces cereviciae* O-31.

When the doughs which had been freeze-stored for a specified period were thawed and baked, the loaves produced by using FD 612 showed a good quality, especially in point of aroma. On the other hand, the loaves produced by using *Saccharomyces cereviciae* O-31 could not give a desirable quality, because the yeasts were freeze-injured.

TABLE 2

| Fermentation before freezing | Frozen dough method | | | | Conventional method | |
| --- | --- | --- | --- | --- | --- | --- |
| | FD 612 | | Baker's yeast | | | |
| | 15 (min) | 90 (min) | 15 (min) | 90 (min) | FD 612 | Baker's yeast |
| Final proof (min) | 58 | 60 | 65 | 120 | 56 | 45 |
| Loaf volume (ml) | 1450 | 1475 | 1300 | 1200 | 1590 | 1600 |
| Appearance (*) | 7.5 | 7.5 | 6.0 | 5.0 | 8.5 | 8.5 |
| Grain (*) | 7.0 | 7.0 | 5.5 | 4.5 | 8.0 | 8.5 |
| Aroma (*) | 7.0 | 7.0 | 5.0 | 4.0 | 7.0 | 7.5 |

(*): Full points are 10

EXAMPLE 2

Sweet goods production using FD 612 was examined according to the following conditions and compared with that using, as a control, commercially available baker's yeast O-31 (Oriental Yeast Co., Ltd.).

| [Formula] | (%) |
| --- | --- |
| Bread flour | 100 |
| Salt | 0.8 |
| Sugar | 25 |
| Shortening | 8 |
| Nonfat dry milk | 2 |
| Yeast food | 0.2 |
| Water | 55 |
| Yeast (FD 612 or O-31) | 6 |

[Procedure]
(1) Mixing:
 1 minute at low speed,
 6 minutes at medium speed,
 2 minutes at high speed.
(2) Dough temperature out of mixer: 24° C.
(3) Fermentation: 15 or 90 minutes (at 28° C.)
(4) Scaling weight: 360 grams
(5) Freezing: 1 hour at −40° C.
(6) Storage: 4 weeks at −20° C.
(7) Thawing: 15 hours at 5° C.
(8) Molding: Immediately after thawing (Dough temperature is 5° C.)
(9) Final proofing: Until a height of 2 cm over from a pan (at 35° C.)

As shown in Table 3, the results were as follows: When the sweet goods were produced in the same manner as conventional bread production method, the loaves produced by using FD 612 showed a quality hardly inferior to that of loaves produced by using conventional *Saccharomyces cerevisiae* O-31.

When the doughs which had been freeze-stored for a specified period were thawed and baked, the sweet goods produced by using FD 612 showed a good quality, especially in point of aroma. On the other hand, the sweet goods produced by using *Saccharomyces cerevisiae* O-31 could not give a desirable quality, because the yeasts were freeze-injured.

TABLE 3

| Fermentation before freezing | Frozen dough method | | | | Conventional method | |
| --- | --- | --- | --- | --- | --- | --- |
| | FD 612 | | Baker's yeast | | | |
| | 15 (min) | 90 (min) | 15 (min) | 90 (min) | FD 612 | Baker's yeast |
| Final proof (min) | 60 | 55 | 65 | 75 | 48 | 35 |
| Loaf volume (ml) | 1400 | 1430 | 1350 | 1280 | 1460 | 1480 |
| Appearance (*) | 7.5 | 7.5 | 6.5 | 6.0 | 8.5 | 8.5 |
| Grain (*) | 7.0 | 7.0 | 6.0 | 5.0 | 8.0 | 8.5 |
| Aroma (*) | 7.0 | 7.0 | 5.5 | 4.5 | 7.0 | 7.5 |

(*): Full points are 10

What is claimed is:
1. A yeast consisting of Saccharomyces species FD 612 (FERM BP-742) having freeze resistance suitable for preparing frozen dough for bread production, and having the following taxonomic properties:
(a) growth state: abundant growth on YM agar medium; a white, flat and smooth colony is formed thereon; a vegetative cell is 2-7μ×2-9μ, circular-elliptic, and multiplicates by budding;
(b) spore formation: ascospores are formed on a potassium acetate medium; a spore is circular;
(c) physiological properties:
 (1) optimum growth condition:
  pH: 4.5–6.0;
  temperature: 28°–30° C.;
  aerobic or anaerobic: facultative aerobic;

(2) conditions for growth:
pH: 2.5–10.0;
temperature: 3°–40° C.;
aerobic or anaerobic: growable under both;
(3) nitrate assimilation: negative;
(4) vitamin requirement: pantothenic acid and biotin are required;
(d) carbon source utilization and fermentation:

| Carbon source | Utilization | Fermentation (Gas production) |
| --- | --- | --- |
| D-arabinose | − | − |
| D-xylose | − | − |
| D-glucose | + | + |
| D-galactose | + | + |
| maltose | + | + |
| sucrose | + | + |
| lactose | − | − |
| melibiose | − | − |
| trehalose | + | ± |
| raffinose | + | ± |
| α-methyl-D-glucoside | + | + |
| dextrin | + | ± |
| soluble starch | + | − |
| ethanol | + | |

± means "positive" in acid production and "negative" in gas production;

(e) the segregation of auxotrophic traits observed:
the segregant strains isolated from Saccharomyces species FD 612 show that the number ratio of strains requiring adenine is about 1:1, and that the number ratio of strains requiring leucine is about 1:1.

2. A process for bread production comprising preparing a dough utilizing flour and Saccharomyces species FD 612 (FERM BP-742) as claimed in claim 1, as the leavening agent, freezing the dough, thawing the dough after freeze storage, and baking the fermented dough.

3. Freeze resistant yeast consisting essentially of Saccaromyces species FD 612 (FERM BP-742).

4. A process for bread production comprising preparing a dough utilizing flour and Saccharomyces species FD 612 (FERM BP-742) as claimed in claim 3, as the leavening agent, freezing the dough, thawing the dough after freeze storage, and baking the fermented dough.

* * * * *